United States Patent [19]

Graves et al.

[11] Patent Number: 5,340,730

[45] Date of Patent: Aug. 23, 1994

[54] PROCESS FOR TRANSFORMING GLADIOLUS

[75] Inventors: Anne C. F. Graves, Bowling Green; Stephen L. Goldman, Toledo, both of Ohio

[73] Assignee: The University of Toledo, Toledo, Ohio

[21] Appl. No.: 900,507

[22] Filed: Jun. 17, 1992

Related U.S. Application Data

[63] Continuation of Ser. No. 652,362, Feb. 7, 1991, abandoned, which is a continuation of Ser. No. 175,709, Mar. 31, 1988, abandoned.

[51] Int. Cl.$^5$ ............................................. C12N 15/00
[52] U.S. Cl. .............................. 438/172.3; 435/240.4; 435/240.45; 435/240.5
[58] Field of Search ............... 435/172.2, 172.3, 240.4, 435/240.45, 240.49, 240.5; 935/18; 536/27, 23.1

[56] References Cited

FOREIGN PATENT DOCUMENTS

WO8600931 2/1986 PCT Int'l Appl. .

OTHER PUBLICATIONS

Wilfret (1971) Proc Ann. Mtg. Florida State Hort. Soc. 84:389–393.
Christou et al. (1986) Plant Physiology 82:218–221.
Krikorian et al. (1986) In/ Cell Culture & Somatic Cell Genetics of Plants, vol. #3, Academic Press pp. 187–205.
"A Time to Engineer," *The Economist*, Mar. 7, 1987, pp. 92–93.
M. Bagdasarian, Lurz, Ruckert, Franklin, M. M. Bagdasarian, Frey, and Timmis, *Gene*, 16, 237 (1981).
Bevan, Barnes, and Chilton, *Nucleic Acids Res.*, 11, 369 (1983).
Boocock and Coggins, *FEBS Letters*, 154, 127 (1983).
Brar, Rambold, Gamborg and Constabel, *Z. Pflanzenphysiol. Bd.*, 95, 377 (1979).
Buchanan-Wollaston, Passiatore and Cannon, *Nature*, 328, 172 (1987).
Byrne, McDonnell, Wright and Carnes, *Plant Cell, Tissue and Organ Culture.* 8, 3–15 (1987).
Bytebier, Deboeck, DeGreve, Van Montagu, and Hernalsteens, *Proc. Acad. Sci USA*, 84, 5345–5349 (1987).
Casse, Boucher, Julliot, Michel and Denaire, *J. Gen. Microbiology*, 113, 229 (1979).
Chee, Klassy & Slightom, *Gene*, 41, 47–57 (1986).
Chilton, Saiki, Yadav, Gordon and Quetier, *Proc. Natl. Acad. Sci. USA*, 77, 4060 (1980).
Coe and Sarkar, *Crop Sci.*, 6, 432 (1966).
Comai, Facciotti, Hiatt, Thompson, Rose and Stalker, *Nature*, 317, 741 (1985).
Crossway, Oakes, Irvine, Ward, Knauf and Shewmaker, *Mol. Gen. Genet.*, 202, 179–185 (1986).
De Cleene, *Phytopath Z*, 113, 81–89 (1985).
De Cleene and De Ley, *The Botanical Review*, 42, 389 (1976).

(List continued on next page.)

Primary Examiner—Gary Benzion
Attorney, Agent, or Firm—Marshall & Melhorn

[57] ABSTRACT

A method of producing a transformed Gladiolus plant comprising: removing a piece of tissue from a corm; inoculating the tissue with vir+ *Agrobacterium tumefaciens*; incubating the inoculated tissue until a tumor forms; culturing at least a portion of the tumor in hormone-free medium until a cormel forms; and growing the cormel to produce the transformed plant. Also, methods of producing a transformed Gladiolus corm or seed comprising growing a transformed Gladiolus plant, prepared as just described, until the corm or seed is formed. Finally, transformed Gladiolus plants, corms and seeds.

4 Claims, 4 Drawing Sheets

OTHER PUBLICATIONS

DeGreve, Dhaese, Seurinck, Lemmers, Van Montagu and Schell, *J. Mol. Appl. Genet.*, 1, 499 (1982).

Depicker, De Wilde, G. De Vos, R. De Vos, Van Montagu and Schell, *Plasmid.* 3. 193 (1980).

Depicker, Stachel, Dhaese, Zambryski and Goodman, *J. Mol. Appl. Genet.*, 1, 561 (1982).

Ditta, Stanfield, Corbin and Helinski, *Proc. Natl. Acad. Sci. USA*, 77, 7347 (1980).

Duncan, Williams, Zehr and Widholm, *Planta*, 165, 322 (1985).

Facciotti, O'Neal, Lee and Shewmaker, *Bio/Technology*, 3, 241 (1985).

FeldmanN, and Marks, *Mol Gen Genet*, 208, 1–9 (1987).

Fraley, Rogers, Horsch, Sanders, Flick, Adams, Bittner, Brand, Fink, Fry, Galluppi, Goldberg, Hoffman and Woo, *Proc. Natl. Acad. Sci., USA*, 80, 4803–4807 (1983).

Fromm, Taylor and Walbot, *Proc. Natl. Acad. Sci. U.S.A.*, 82, 5824–5828 (1985).

Fromm, Taylor and Walbot, *Nature*, 319, 791 (1986).

Graves, Ph.D. Dissertion, Bowling Green State University (1982).

Graves and Goldman, Abstract of seminar presented at the Crown Gall Conference held on Sep. 11–15, 1986.

Graves and Goldman, *Journal of Bacteriology*, 169, 1745 (1987).

Grimsley, T. Hohn, Davies, and B. Hohn, *Nature*, 325, 177 (1987).

Grimsley, Ramos, Hein, and B. Hohn, *Bio/Technology*, 6, 185 (1988).

Hain, Stabel, Czernilofsky, Steinbib, Herrara-Estrella, Schnell, *Mol. Gen. Genet.*, 199, 161–168 (1985).

Hernalsteens, Thia-Toong, Schell and Van Montagu, *The EMBO J.*, 3, 3039 (1984).

Hooykaas-Van Slogteren, Hooykaas and Schilperoort, *Nature*, 311, 763 (1984).

Kado and Liu, *Journal of Bacteriology*, 145, 1365 (1981).

Kao, Perry and Kado, *Mol. Gen. Genet.*, 188, 425 (1982).

Klein, Wolf, Wu and Sanford, *Nature*, 327, 70 (1987).

Korohoda and Strzalka, *Z. Pflanzenphysiol Bd.*, 94, 95–99 (1979).

Krens, Molendijk, Wullems and Schilperoort, *Nature*, 296, 72 (1982).

Kyozuka, Hayashi and Shimamoto, *Mol. Gen. Genet.*, 206, 408–413 (1987).

Lin and Kado, *Can. J. Microbiol.*, 23, 1554 (1977).

J. Lippincott, Margo and B. Lippincott, *J. Bact.*, 132, 824 (1977).

J. Lippincott, Webb and B. Lippincott, *J. Bact.*, 90, 1155 (1965).

Lorz, Baker and Schell, *Mol. Gen. Genet.*, 199, 178–182 (1985).

Lundquist, Close, and Kado, *Mol. Gen. Genet.*, 193, 1–7 (1984).

Marton, Wullems, Molendijk and Schilperoort, *Nature*, 277, 129 (1979).

Matthysse, *J. Bact.*, 154, 906 (1983).

Morgun, Chernykh, Kordyum, *Chem. Abstracts*, 88(11), 71618k (1977) (*Mol. Biol.*) (*Kiev*), 18, 50 (1977)).

Murai, Sutton, Murray, Slightom, Merlo, Reichert, Sengupta-Gopalan, Stock, Barker, Kemp and Hall, *Science*, 222, 476 (1983).

Murashige and Skoog, *Physiol. Plant*, 15, 473 (1962).

Nester, Gordon, Amasino and Yanofsky, *Ann. Rev. Plant Physiol.*, 35, 387 (1984).

Ohta, *Proc. Natl. Acad. Sci. USA*, 83 715–719 (1986).

Otten, De Greve, Hernalsteens, Van Montagu, Schieder, Straub and Schell, *Mol. Gen. Genet.*, 183, 204–213 (1981).

Otten and Schilperoort, *Biochem. Biophys. Acta*, 527, 497 (1978).

Otten, Vreugdenhil and Schilperoort, *Biochem. Biophys. Acta*, 485, 268 (1977).

Owens and Cress, *Plant Physiol.*, 77, 87–94 (1985).

De la Pena, Lorz and Schell, *Nature*, 325, 274 (1987).

de la Pena, Puertas and Merino, *Chromosoma (Berl.)*, 83, 241 (1981).

Paszkowski, Shillito, Saul, Mandak, T. Hohn, B. Hohn and Potrykus, *The EMBO J.*, 3, 2717 (1984).

"Plant Genetic Engineering Gets A New Tool," *Chemical & Engineering News*, Jul. 13, 1987, p. 21.

Potrykus, Harms and Lorz, *Theor. Appl. Genet.*, 54, 209 (1979).

Potrykus, Saul, Petruska, Paszkowski and Shillito, *Mol. Gen. Genet.*, 199, 183 (1985).

Rao, B. Lippincott and J. Lippincott, *Physiol. Plant.*, 56, 374 (1982).

Sass, *Corn and Corn Improvement*, 89–110 (G. F. Sprauge, ed., 1955).

Schafer, Gorz and Kahl, *Nature*, 327, 529 (1987).

Sciaky, Montoya and Chilton, *Plasmid*, 1, 238 (1978).

(List continued on next page.)

OTHER PUBLICATIONS

Slightom, Sun and Hall, *Proc. Nat'l Acad. Sci. USA*, 80, 1897 (1983).
Stalker, Hiatt and Comai, *The J. Biol. Chem.*, 260, 4724 (1985).
Stonier, *J. Bacteriol.*, 79, 889 (1960).
Thomashow, Nutter, Postle, Chilton, Blattner, Powell, Gordon and Nester, *Proc. Natl. Acad. Sci. USA*, 77, 6448 (1980).
Toole, *Amer. Jour. Bot.*, 11, 325 (1924).
Turgeon, Wood and Braun, *Proc. Natl. Acad. Sci. USA*, 73, 3562 (1976).
Waldron, Murphy, Roberts, Gustafson, Armour and Malcolm, *Plant Molecular Biology*, 5, 103 (1985).
J. D. Watson, J. Tooze & J. T. Kurtz, *Recombinant DNA*, pp. 164–175 (1983).
Yadav, Postle, Saiki, Thomashow and Chilton, *Nature*, 287, 458 (1980).
Yamada, Zhi-Qi and Ding-Tai, *Plant Cell Reports*, 5, 85 (1986).
Abbe, and Stein, *Amer. Journ. Bot.*, 41, 285 (1954).
Abdullah, Cocking and Thompson, *Bio/Technology*, 4, 1087 (1986).
Abel, Nelson, De, Hoffman, Rogers, Fraley and Beachy, *Science*, 232, 738 (1986).
An, Watson, Stachel, Gordon, and Nester, *The EMBO Journal*, 4, 277–284 (1985).

RESTRICTION SITE AND FUNCTION MAP
OF PLASMID pCEL30
(7.15 kb)

RESTRICTION SITE AND FUNCTION MAP
OF PLASMID pCEL44
(17.5 Kb)

PROCESS FOR TRANSFORMING GLADIOLUS

This application is a continuation of application Ser. No. 07/652,362, filed Feb. 7, 1991, now abandoned, which is a continuation of Ser. No. 07/175,709 filed Mar. 31, 1988, now abandoned.

BACKGROUND OF THE INVENTION

Virulent strains of the soil bacterium *Agrobacterium tumefaciens* are known to infect dicotyledonous plants and to elicit a neoplastic response in these plants. The tumor-inducing agent in the bacterium is a plasmid that functions by transferring some of its DNA into its host plant's cells where it is integrated into the chromosomes of the host plant's cells. This plasmid is called the Ti plasmid, and the virulence of the various strains of *A. tumefaciens* is determined in part by the vir region of the Ti plasmid which is responsible for mobilization and transfer of the T-DNA. The T-DNA section is delimited by two 23-base-pair repeats designated right border and left border, respectively. Any genetic information placed between these two border sequences may be mobilized and delivered to a susceptible host. Once incorporated into a chromosome, the T-DNA genes behave like normal dominant plant genes. They are stably maintained, expressed and sexually transmitted by transformed plants, and they are inherited in normal Mendelian fashion.

The lump of plant tumor tissue that grows in an undifferentiated way at the site of the *A. tumefaciens* infection is called a crown gall. Cells of crown gall tumors induced by *A. tumefaciens* synthesize unusual amino acids called opines. Different strains of *A. tumefaciens* direct the synthesis of different opines by the crown gall cells, and the particular opine induced is a characteristic of the strain which infected the plant. Further, the ability to catabolize the particular opine induced by a given strain is characteristic of that strain.

Opines are not normally synthesized by *A. tumefaciens* or by the uninfected host plants. Although it is the T-DNA which codes for the enzymes involved in the synthesis of the opines, the opine synthases, these genes are expressed only in infected plant tissue. This type of expression is consistent with the observation that these genes are under the control of eukaryotic regulatory sequences on the T-DNA.

The most common opines are octopine and nopaline. The opine synthase that catalyzes the synthesis of octopine is lysopine dehydrogenase, and the opine synthase that catalyzes the synthesis of hopaline is hopaline dehydrogenase.

When crown gall cells are put into culture they grow to form a callus culture even in media devoid of the plant hormones that must be added to induce normal plant cells to grow in culture. A callus culture is a disorganized mass of relatively undifferentiated plant cells. This ability of crown gall cells to grow in hormone-free media is also attributable to the presence of the T-DNA in the transformed host plant cells since genes which direct the synthesis of phytohormones are also associated with the T-DNA.

A DNA segment foreign to the *A. tumefaciens* and to the host plant which is inserted into the T-DNA by genetic manipulation will also be transferred to host plant's cells by *A. tumefaciens*. Thus, the Ti plasmid can be used as a vector for the genetic engineering of host plants. Although, in wild type *A. tumefaciens* there is only one Ti plasmid per bacterium, in genetically-engineered *A. tumefaciens*, the vir region and the T-DNA do not have to be carried on the same Ti plasmid for transfer of the T-DNA to occur. The vir region and the T-DNA can be carried on separate plasmids contained within the same Agrobacterium.

It has been assumed that the host range of *A. tumefaciens* was limited to the dicotyledons, and that transformation of monocotyledons generally could not be effected with this bacterium. For instance, DeCleene and DeLey in *The Botanical Review*, 42, 389 (1976) reported the results of an extensive study of the plant host range of *A. tumefaciens*. Their article teaches that certain strains of the monocot orders Liliales and Arales are susceptible to infection with *A. tumefaciens*, but that monocotyledons in general are not susceptible to such infections. Susceptibility to *A. tumefaciens* infection was determined by whether a swelling or tumor developed at the wound site.

More recently, Hernalsteens et al. reported in *The EMBO Journal*, 3, 3039 (1984) that cultured stem fragments of the monocotyledon *Asparagus officinalis*, a member of the family Liliaceae, infected with *A. tumefaciens* strain C58 developed tumorous proliferations. One of these tumorous proliferations could be propagated on hormone-free medium, and opines were detected in the established callus culture derived from this tumorous proliferation.

Hooykaas-Van Slogteren et al., in *Nature*, 311, 763 (1984), reported the production of small swellings at wound sites infected with *A. tumefaciens* on monocotyledons of the Liliaceae and Amaryllidaceae families. Opines were detected in plant cells taken from the wound sites of the infected plants.

In 1982, Anne C. F. Graves reported in her Ph.D. dissertation entitled "Some Tumorigenic Activities of *Agrobacterium Tumefaciens* (Smith and Town) Conn." (Bowling Green State University) that irregular masses of tissue developed on Gladiolus disks in response to inoculations with *A. tumefaciens* C58N and B6. These masses of tissue appeared to be the same as, and to have cellular morphology similar to, those that developed on potato tuber disks inoculated with these same bacteria. Gladiolus is a member of the monocotyledonous Iridaceae family. A compound that co-migrated with the octopine standard during electrophoresis was found in the proliferations on the Gladiolus disks that were induced by strain B6, and one that migrated just behind the octopine standard occurred in those induced by C58N. Also, octopine dehydrogenase was found in extracts of the cellular proliferations induced by *A. tumefaciens* B6, but not in those induced by *A. tumefaciens* C58N.

Dr. Graves also described the response of certain other monocots to inoculation with *A. tumefaciens*. No cellular proliferation was observed on ginger root rhizome disks, and the results with tulip bulb disks were inconclusive. Cellular proliferations on disks of the rhizomes of cattail and skunk cabbage were limited to several layers of clear cells at the ends of vascular bundles in the early spring.

More recently, Graves and Goldman, in *Proceedings Of The Crown Gall Conference*, p. 20 (September 1986), reported that tumors developed on disks of Gladiolus corms in response to infection with vir+ *A. tumafaciens*, but not avirulent *A. tumefaciens*. These tumors produced opines and could grow on medium in the absence of auxin.

Graves and Goldman, in *Plant Mol. Biol.* 7, 43–50 (1986), have also reported the transformation of seedlings of the monocot *Zea mays* by *A. tumefaciens*.

Lorz et al. in *Mol. Gen. Genet.* 199, 178 (1985), Fromm et al. in *Nature,* 319, 791 (1986) and Portrykus et al. in *Mol. Gen. Genet*, 199, 183 (1985) have reported the transformation of Gramineae by direct gene transfer to protoplasts. Protoplasts are plant cells from which the cell wall has been removed by digestion with enzymes. Lorz et al. transformed protoplasts of *Triticum monococcum* using a DNA construct containing the nopaline synthase promotor and the polyadenylation regulatory signal of the octopine synthase gene. Fromm et al discloses that the electropotation-mediated transfer of plasmid pCaMVNEO (comprising the cauliflower mosaic virus 35 S promoter, the neomycin phosphotransferase II gene from the transposon Tn5 and the nopaline synthase 3' region) into maize protoplasts results in stably-transformed maize cells that are resistant to kanamycin.

Finally, PCT International Publication No. WO 86/00931 Simpson et al published Feb. 13, 1986, teaches in vivo methods of transforming and regenerating intact plants. This patent application teaches that the methods of the invention can be used for the transformation of any plant that forms a shooty tumor following infection with an *A. tumefaciens* shooty mutant strain.

SUMMARY OF THE INVENTION

According to the present invention, there now provided a method of producing a transformed Iridaceae plant comprising: removing a piece of tissue from a corm; inoculating it with vir+ *A. tumefaciens;* incubating the inoculated tissue until a tumor forms; culturing at least a portion of the tumor in hormone-free medium until a cormel is formed; and growing the cormel to produce the transformed plant. Transformed Iridaceae corms and seeds can be produced by growing a transformed plant, prepared as just described, until the seeds and corms are formed. In the preferred practice of the invention, vir+ *A. tumefaciens* containing a vector comprising genetically-engineered T-DNA is used.

In addition, the invention comprises a transformed Iridaceae plant, corm and seed. The transformed Iridaceae plant, corm or seed may be derived from corm tissue infected with vir+ *A. tumefaciens,* preferably with vir+ *A. tumefaciens* that contains a vector comprising genetically-engineered T-DNA. The invention also comprises transformed Iridaceae plants, corms and seeds whose cells contain a segment of T-DNA, preferably a segment of genetically-engineered T-DNA.

The invention is clearly useful since it provides a method for transforming Iridaceae that results in the production of transformed corms, seeds and whole plants. Thus, the invention provides, for the first time, a method of transforming Iridaceae which allows for the expression of exogenous DNA in agriculturally important forms or parts of the Iridaceae. The invention allows for the development of strains of Iridaceae having altered or superior traits, such as strains having unique colors or color patterns or strains having tolerance to disease, by providing a means whereby exogenous DNA coding for such traits can be incorporated into Iridaceae plants, corms and seeds.

DETAILED DESCRIPTION OF THE PRESENTLY PREFERRED EMBODIMENTS

Figure 1:
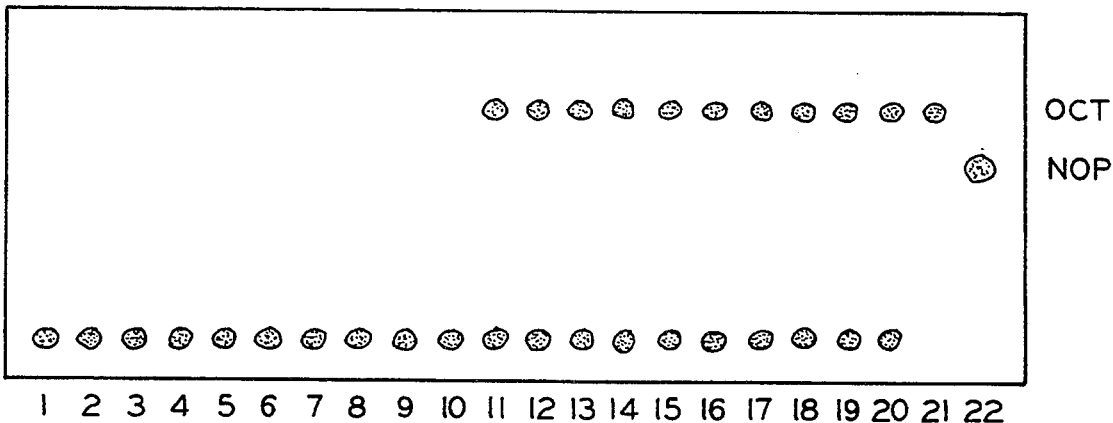
FIG. 1 is a drawing of developed paper electrophoretogram which shows the results of the electrophoresis of the products produced by incubating cellfree extracts of individual tumors excised from Gladiolus corms inoculated with *A. tumefaciens* strain B6 with a reaction medium containing reagents which allow for the detection of lysopine dehydrogenase enzyme activity. Certain controls were also electrophoresed.

According no the invention, there is provided a method of producing transformed Iridaceae plants, corms and seeds comprising inoculating a piece of tissue taken from the corm of a member of this family with vir+ *A. tumefaciens*. In the preferred practice of the method of the invention, the corm is sterilized, the top and bottom of the corm are sterilely cut off and discarded, a core of tissue is sterilely cut from the remaining corm using a cork borer, and disks of tissue are sterilely cut from the core using a razor blade.

The term Iridaceae, as used herein, is meant to include all of the forms and parts of the Iridaceae, including plants, corms, seeds, leaves and stalks. "Transformed" is used herein to mean genetically modified by the incorporation and expression of exogenous DNA. "Exogenous DNA" is DNA not normally found in the strain of Iridaceae which is to be transformed. Exogenous DNA may be obtained from prokaryotic or eukaryotic sources, including strains of Iridaceae other than the one to be transformed.

The pieces of corm tissue are inoculated by dripping a solution of vir+ *A. tumefaciens* onto them. Vir+ *A. tumefaciens* are bacteria that are capable of mobilizing and transferring T-DNA into host plant cells, and an *A. tumefaciens* carrying a plasmid, whether natural or engineered, coding for these functions is vir+. Thus, a strain of *A. tumefaciens* that carries a wild-type Ti plasmid is vir+ and can be used in the present invention. Many such strains are known and are publicly available. See e.g., American Type Culture Collection Catalogue (ATCC) of Strain I, p. 66 (15th edition, 1982). The vir+ region of a wild type Ti plasmid can be used to mobilize and transfer T-DNA on the same Ti plasmid or to deliver T-DNA on another plasmid contained in the same bacterium. In addition, the mobilization and transfer functions can be supplied by helper plasmids. Such helper plasmids have been described by Ditta et al. in PNAS, 77, 7347 (1980) and by Bagdasarian et al. in *Gene,* 16, 237 (1981). Thus, a strain of *A. tumefaciens* that carries a helper plasmid is also vir+. Finally, the mobilization and transfer functions may be coded on the same engineered plasmid that contains the T-DNA, and bacteria containing such a plasmid are also vir+.

The T-DNA transferred by the vir+ *A. tumefaciens* may be native T-DNA or may preferably be genetically-engineered T-DNA. Genetically-engineered T-DNA is a DNA construct comprising T-DNA border sequences, a heterologous gene and a transcription unit connected in operable order. Methods of preparing such constructs are known in the art.

A heterologous gene is a gene which is not normally found in the T-DNA and which is also not normally found in the DNA of the strain of Iridaceae which is to be transformed. Heterologous genes may be isolated from prokaryotic and eukaryotic sources, including strains of Iridaceae other than the one to be transformed. Of particular interest are those heterologous genes which confer agronomically significant traits on plants containing them such as the maize transposable genes A, C, D, S, SPM, genes conferring vital resistance and genes that regulate pigment synthesis.

The heterologous gene is flanked by a transcription unit containing, e.g., promotors and terminators, which allow for expression of the heterologous gene in the strain of Iridaceae to be transformed. The heterologous gene-transcription-unit construct is flanked by the border sequences. Any T-DNA border sequence, native or synthesized, can be used to flank the heterologous-gene-transcription-unit construct as long as the border sequence functions to intearate the heterologous gene into the cell genome of the strain of Iridaceae to be transformed. The genetically-engineered T-DNA is linked to a DNA fragment containing a replicon that is functional in Agrobacterium to form a vector.

After the tissue pieces are inoculated with the vir+ *A. tumefaciens*, they are incubated until a tumor has formed, at which time at least a portion of the tumor is transferred sterilely to hormone-free medium. As used herein, "tumor" means tumors, masses swellings, growths and other types of cellular proliferations.

The tumor tissue is allowed to grow on the hormone-free medium until a callus culture is established and the callus culture produces cormels. These cormels are planted and allowed to grow into whole plants which are able to reproduce sexually and by vegetative propagation to form seeds and corms. Those skilled in the art will recognize that various and numerous progeny carrying the trait coded for by the exogenous DNA can be produced using known breeding techniques.

EXAMPLES

Example I

A. preparation of Bacteria

A single colony of the *A. tumefaciens* strain B6 was inoculated into a yeast extract broth (YEB) containing 0.1% yeast extract, 0.8% nutrient broth and 0.5% sucrose dissolved in water. The yeast extract and nutrient broth were purchased from Difco Laboratories, Detroit, Mich. The sucrose was purchased from either Fisher Scientific, Detroit, Mich., or Sigma, St. Louis, Mo. The bacteria were incubated in the YEB for 48 hours at 27° C. in a shaking water bath or until such time as they had reached a final concentration of $3.8 \times 10^9$ cells per milliliter.

The B6 strain is a standard wild type strain of *A. tumefaciens*. It is virulent (vir+) and it codes for the production of lysopine dehydrogenase in suitable plant hosts. It was obtained from James and Barbara Lippincott, Northwestern University, Evanston, Ill. Some of its properties have been described in Stonier, *J. Bact.*, 79, 889 (1960). The B6 strain is also on deposit at the American Type Culture Collection (ATCC), Rockville, Md., and it has been given accession number 23308.

B. Preparation of Gladiolus Disks

Corms of the Gladiolus cultivar Oscar were obtained from The Andersons, Maumee, Ohio. This variety is a standard variety which is available commercially.

The corms were sterilized using the following procedure. The corms were scrubbed with a vegetable brush and soaked for 20 minutes in 5% sodium hypochlorite solution containing 2 ml of Ajax dishwashing detergent/100 ml of sodium hypochlorite solution. The ends were cut from the corms with a knife that was sterilized by dipping it into alcohol and flaming it. Cores of tissue were taken from the corms with sterile cork borers. Cores ranged in diameter from 1.8 mm (No. 11 borer) to 2.1 mm (No. 13). The cores were cut into disks approximately 0.5 mm thick with a sterile razor blade. The first and last disks of each core were discarded.

C. Inoculation Of Disks With Bacteria

The disks, picked at random from many cores, were placed in sterile $100 \times 20$ mm Petri dishes containing 25 ml of 2% agar (20 gram of Difco agar per liter water, sterilized for 15 min at 15 lbs/in$^2$ pressure). Five disks were placed equidistantly from each other around the perimeter of the dishes. Each disk was inoculated with 0.1 ml of a $10^9$ cells per milliliter bacterial suspension. The inoculated disks were incubated at 25° C.

D. Results

1. Observation Of Disks: Twenty-four days after inoculation of the surface of the disks, tumors were observed growing on approximately 50% of the disks inoculated with vir+ *A. tumefaciens* strain B6.

2. Assay For Enzyme Activity in Tumors: Once the tumors reached approximately 1 cm in size (30 days post inoculation), a portion of each tumor was excised and homogenized in a 0.1M Tris-HCl buffer, pH 8.0, containing 0.5M sucrose, 0.1% (weight/volume) ascorbic acid and 0.1% (weight/volume) cysteine-HCl, using a Wheaton tissue grinder, until the homogenate had a homogeneous consistency. Next, the homogenates were spun in a Fisher Microfuge at $13,000 \times g$ for two minutes to obtain cell-free extracts.

A portion of the cell-free extract was added to an equal volume of a reaction medium designed to detect lysopine dehydrogenase activity. This reaction medium consisted of 30 mM L-arginine, 75 mM pyruvate and 20 mM NADH dissolved in 0.2M sodium phosphate buffer, pH 7.0. The enzyme reaction was allowed to proceed at room temperature for the times indicated below.

The products of the enzyme reaction were separated electrophoretically on Whatman 3 MM paper. At the start of the enzyme reaction period (time zero), a 5 ul sample of the reaction mixture was spotted at the anodal site on the paper and dried. After 15 hours of reaction, another 5 ul sample of the reaction mixture was spotted on the paper and dried. Finally, a 5 ul sample of a 100 ug/ml solution of synthetic octopine purchased from Calbiochem, Division of American Hoescht, La Jolla, Calif. and a 5 ul sample of 100 ug/ml solution of synthetic nopaline purchased from Sigma, St. Louis, Mo., were spotted on the paper and dried.

Electrophoresis was performed in a formic acid (90.8%)/glacial acetic acid/water (5:15:80, volume/volume) solution, pH 1.8, for 2.5 hours at 450 volts. The paper was dried and then stained by dipping it into a solution containing one part 0.02% (weight/volume) phenanthrenequinone in absolute ethanol plus one part 10% (weight/volume) NaOH in 60% (volume/volume) ethanol. After drying, the spots were visualized under an ultraviolet lamp at 366 nm.

The results of the electrophoresis of the products produced by adding the cell-free extracts of single tumors that grew on B6-inoculated corm disks to lysopine dehydrogenase reaction medium are shown in FIG. 1. In that figure, lanes 1–10 contain samples of the reaction mixture produced by adding a portion of the cell-free extract of individual tumors that grew on ten B6-inoculated Gladiolus corm disks to an equal volume of the lysopine dehydrogenase reaction medium at time zero, lanes 11–20 contain the products produced by incubating a portion of the cell-free extract of individual tumors that grew on ten B6-inoculated Gladiolus corm disks with an equal volume of lysopine dehydrogenase reaction medium for fifteen hours, lane 21 contains synthetic octopine, and lane 22 contains synthetic hopaline.

The results shown in FIG. 1 demonstrate that octopine production is caused by cell-free extracts of the tumors produced by B6-inoculated Gladiolus corm disks, lanes 11–20. Furthermore, the amount of octopine produced, as measured by an increase in phenanthrenequinone fluorescence, increases in proportion to the time of incubation. While no octopine can be detected at time zero, lanes 1–10, it is clearly present after fifteen hours of incubation, lanes 11–20. Such results are in accord with the proposition that the reaction is enzyme catalyzed and that the enzyme extracted from the tumors growing on B6-infected corm disks is lysopine dehydrogenase. Since transformed plant tissues are known to express the opine synthase genes, these results are also in accord with the proposition that the corm tissue has been transformed by infection with the vir+ *A. tumefaciens* strain B6.

Example II

Example I was repeated using Gladiolus cultivars Carmen, White Prosperity, White Friendship, Yellow Emperor and Golden Monarch. These varieties are all standard varieties that are available commercially. They were all obtained from The Andarsons, Maumee, Ohio.

Tumors were observed growing on B6-inoculated disks of each variety. The cell-free extracts of these tumors caused octopine production when added to lysopine dehydrogenase reaction medium, and these results are in accord with the proposition that the corm tissue of each of these varieties was transformed by infection with vir+ *A. tumefaciens* strain B6.

Example III

A. Preparation of Bacteria

A single colony of the *A. tumefaciens* strain C58 was inoculated into YEB, and the bacteria were incubated as described above in Example I, part A, for strain B6. The C58 strain is a standard wild type strain of *A. tumefaciens*. It is vir+, and it codes for +the production of nopaline dehydrogenase in suitable plant hosts. It was obtained from James and Barbara Lippincott, Northwestern University, Evanston, Ill., or from Clarence Kado, University of California, Department of Plant Pathology, Davis, Calif. It has been described in Depicker et al, Plasmid, 3, 193 (1980) and Kao, et al, *Molec. Gen. Genet.*, 188, 425 (1982). Strain C58 is also on deposit at the ATCC and has been given accession number 33970.

B. Transformation of Gladiolus

Corms of the Gladiolus cultivar White Prosperity were sterilized, cut into disks, inoculated and incubated as described above in Example I, parts B and C, except that the corm disks were inoculated with strain C58 rather than strain B6.

C. Results

1. Observation of Disks: Twenty-five days after inoculation of the disks, tumors were observed growing on the surface of about 65% of the disks inoculated with vir+ *A. tumefaciens* strain C58.

2. Assay For Enzyme Activity in Tumors: Once the tumors reached approximately 1 cm in size (30 days post inoculation), a portion of each of the tumors was excised, homogenized and assayed for enzymatic activity as described above in Example I, part D, except that the reaction medium used was the one designed to assay for hopaline dehydrogenase activity. This reaction medium consisted of 60 mM L-arginine, 60 mM $\alpha$-ketoglutaric acid and 16 mM NADH dissolved in 0.2M sodium phosphate buffer, pH 7.0.

Figure 2:
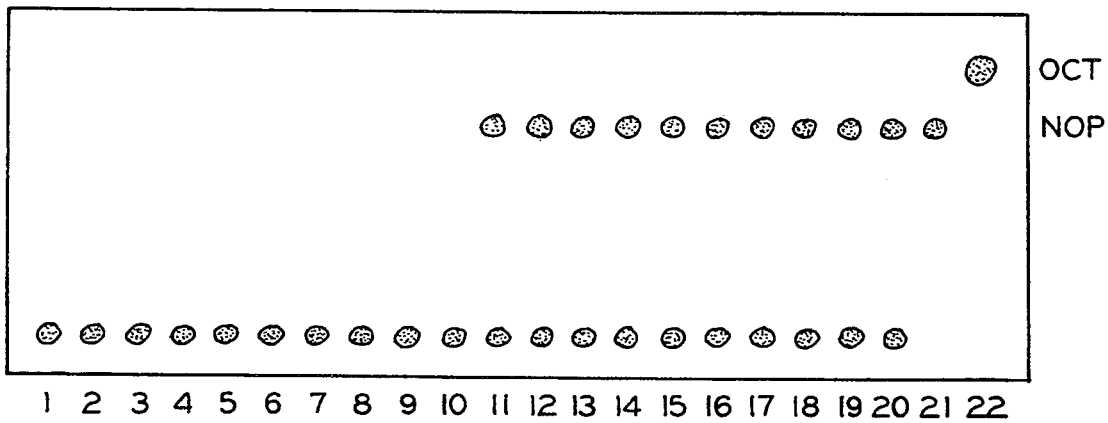
FIG. 2 is a drawing of a developed paper electrophoretogram. The materials electrophoresed were produced by the catabolism by certain strains of *A. tumefaciens* of the products produced by incubating cell-free extracts of individual tumors produced by corms inoculated with *A. tumefaciens* strain C58 with nopaline dehydrogenase reaction medium. Certain controls were also electrophoresed.

The results are shown in Finite 2. Lanes 1–10 in FIG. 2 contain the product produced by mixing a portion of the cell-free extract of individual tumors that grew on ten C58-inoculated corm disks with an equal volume of hopaline dehydrogenase reaction medium at time zero, lanes 11–20 contain the product produced by incubating a portion of the cell-free extract of individual tumors that grew on ten C58-inoculated corm disks with an equal volume of hopaline dehydrogenase reaction medium for fifteen hours, lane 21 contains synthetic hopaline, and lane 22 contains synthetic octopine. Thus, FIG. 2 shows that hopaline is produced by the cell-free extracts of the tumors that grew on the C58-inoculated Gladiolus corm disks, lanes 11–20. Once again, the amount of hopaline produced, as measured by an increase in phenanthrenequinone fluorescence, increased in proportion to the length of the incubation time, and such results are in accord with the proposition that the reaction is enzyme-catalyzed and that the enzyme extracted from the tumors growing on C58-infected corm disks is nopaline dehydrogenase. Since transformed plant tissues are known to express the opine synthase genes, these results are also in accord with the proposition that the Gladiolus corm tissue has been transformed by infection with the vir+ *A. tumefaciens* strain C58.

Example IV

Example III was repeated using Gladiolus cultivars Oscar, Carmen, White Friendship, Yellow Emperor and Golden Monarch. Tumors were observed growing on C58-inoculated disks of each variety. The cell-free extracts of these tumors caused nopaline production when added to hopaline dehydrogenase reaction medium. These results are in accord with the proposition that the corm tissue of each of these varieties was transformed by infection with vir+ *A. tumefaciens* strain C58.

Example V

A. Growth On Hormone-Free Medium

Portions of tumors growing on Gladiolus corm disks prepared, inoculated and incubated as described in Example III, parts A and B, were transferred axenically onto Murashige-Skoog medium (described in *Physiol. Plant,* 15 473–97 (1962)) containing vancomycin and carbenicillin at 100 μg/ml each, but lacking auxin and cytokinin. The tumors continued to grow on this medium and formed callus cultures. After five months, shoots differentiated from some of the masses.

B. Production Of Plants

Two months after beginning to culture the tumors on the hormone-free medium as described in part A of this example, cormels were produced by the bacteria-free calli. The cormels were planted in pots containing potting soil and grown into whole plants.

C. Assays

Figure 3:
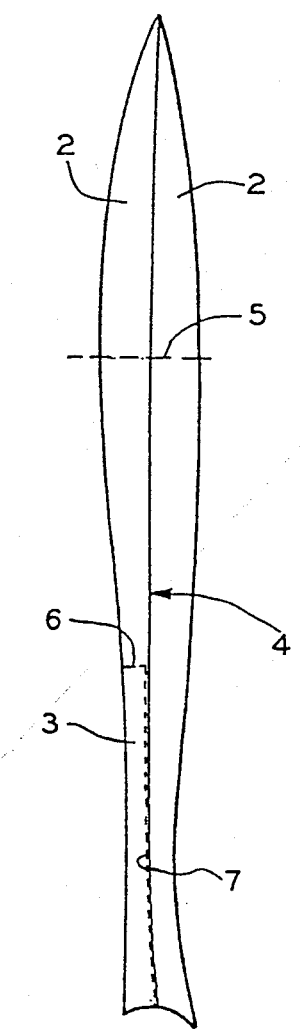
FIG. 3 is a diagram of a leaf.

1. Assay For Enzymatic Activity in Leaves: Leaves of the Gladiolus plants grown from the cormels as described in part B of this example were assayed for the presence of hopaline dehydrogenase 8 weeks after the planting of the cormels. To perform the assay, sections were dissected out of the leaves, and the dissected sections from each leaf were homogenized together in Tris-HC1 buffer, centrifuged and assayed for enzymatic activity as described above in Example III, part C. The sections of the leaves which were used for the assay are indicated by the numerals 2 and 3 in FIG. 3. The section designated by the numeral 3 was dissected by cutting along lines 6 and 7. Line 7 is coincident with the midrib 4 of the leaf. Section 3 is located at the base of the leaf which is normally attached to the plant. The base of the leaf is the growing end of the leaf, and this area contains the newest cells on the leaf. The sections designated by the numeral 2 were dissected by cutting along line 5 which is perpendicular to the midrib 4. Sections 2, 2 are at the tip of the leaf, and they contain the oldest cells on the leaf. Each section 2 or 3 constitutes about 1/6 of the leaf's surface area.

Figure 4:
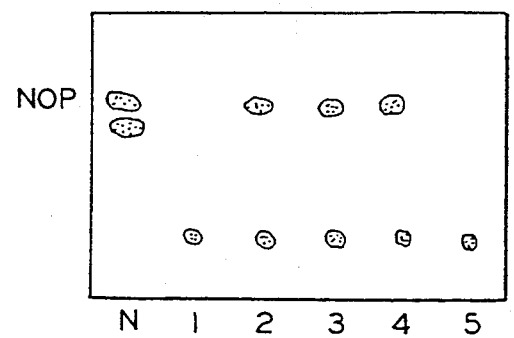
FIG. 4 is a drawing of a developed electrophoretogram showing the results of the electrophoresis of the products produced by incubating the cell-free extracts of the dissected sections of four leaves from four separate plants grown from the cormels produced by the tumors that grew on C58-inoculated Gladiolus corm disks with nopaline dehydrogenase reaction medium.

The results of the electrophoresis of the product produced by incubating the cell-free extracts of these sections of 4 leaves taken from 4 separate plants with hopaline dehydrogenase reaction medium are shown in FIG. 4. In FIG. 4, lane 1 contains nopaline dehydrogenase reaction medium, and lanes 2–5 contain the products produced by incubating the cell-free extracts of the leaves with hopaline dehydrogenase medium for twelve hours. As shown there, cell-free extracts of 3 out of 4 leaves produced nopaline demonstrating that they contained nopaline dehydrogenase activity. Since these leaves are derived from the callus cultures by cell division and differentiation, these results demonstrate that the cells from the tumors formed on the inoculated corm disks were able to pass on the ability to synthesize nopaline dehydrogenase to future generations of cells. Thus, these results demonstrate that transformation of cells in the inoculated corm tissue and of cells derived from these cells has taken place.

2. Assay For Enzymatic Activity In Corms: The plants prepared in part B of this example are allowed to grow until they produce corms by vegetative propagation. These corms are sterilized and cut into disks as described in Example I, part B, except that no inoculation takes place. The disks are homogenized, centrifuged and assayed for enzymatic activity as described in Example III, part C. The cell-free extracts of these corm disks produce nopaline when added to hopaline dehydrogenase reaction medium, demonstrating that they are transformed.

3. Assay For Enzymatic Activity In Pollen: The plants prepared in Dart B of this example are grown until they produce pollen. Samples of the pollen are assayed for the presence of nopaline dehydrogenase. To perform the assay, 0.5 to 1.0 ml pollen is homogenized in Tris-HC1 buffer, centrifuged and assayed for enzymatic activity as described in Example III, part C. The pollen produced by the transformed plants contains nopaline dehydrogenase activity, demonstrating that transformation takes place.

4. Assay For Enzymatic Activity In Leaves Of Plants Derived From Transformed Pollen: Transformed pollen, identified as described above in part C3 of this example, is used to fertilize plants grown from uninfected White Prosperity corms. The seeds produced by the fertilized plants as a result of this mating are harvested and planted in pots containing potting soil.

The seeds are allowed to grow into plants and leaves are taken from the plants and assayed for hopaline dehydrogenase activity as described above in part C1 of this example. Cell-free extracts of the leaves produce hopaline when incubated with nopaline dehydrogenase medium, showing the leaves are transformed.

Example VI

A single colony of the *A. tumefaciens* strain LBA 4013 was inoculated into YEB, and the bacteria were incubated as described above in Example I, part A, for strain B6. The LBA 4013 strain is a mutant strain derived from *A. tumefaciens* strain Ach5. LBA 4013 contains the wild type Ti plasmid pTiAch5 which is vir+, and LBA 4013 codes for the production of lysopine dehydrogenase in suitable plant hosts. LBA 4013 was obtained from Clegg Waldron, Eli Lilly and Co., Indianapolis, Ind. It has been described by Marton et al., in *Nature* 277, 129 (1979).

Corms of the Gladiolus cultivar Carmen were sterilized and cut into disks that were inoculated and incubated as described above in Example I, parts B and C, except that the disks were inoculated with strain LBA 4013, rather than strain B6.

Tumors were found to grow on about 40% of the inoculated corm disks. When the tumors had reached about 1 cm in size, they were assayed for enzyme activity as described above in Example I, part D. Using this procedure, octopine production by cell-free extracts of the tumors that grew on the LBA 4013-inoculated corm disks was demonstrated, showing that the corm tissue was transformed.

Example VII

Example VI was repeated using Gladiolus cultivars Oscar, White Prosperity, White Friendship, Yellow Emperior and Golden Monarch. Tumors were observed growing on LBA 4013-inoculated disks of each variety. The cell-free extracts of these tumors caused octopine production when added to lysopine dehydrogenase reaction medium, indicating that the corm tissue of each variety had been transformed by infection with vir+ *A. tumefaciens* strain LBA 4013.

Example VIII

A. Preparation of Bacteria

A single colony of the *A. tumefaciens* strain CA19 was inoculated into YEB, and the bacteria were incubated as described above in Example I, Part A, for strain B6. The CA19 strain is derived from strain LBA 4013 and contains the pTiAch5 plasmid of LBA 4013 which is vir+, as described above in Example IV, and strain CA19 codes for the production of lysopine dehydrogenase in suitable plant hosts.

Strain CA19 also contains the micro-Ti plasmid pCEL44. Micro-plasmid pCEL44 comprises a construct consisting of the gene coding for hygromycin phosphotransferase (aphIV) inserted between the 5' promoter and associated amino terminal region-encoding sequence of an octopine synthase gene and the 3'terminator sequence of a hopaline synthase gene. This construct is assembled between T-DNA border fragments in broad-host-range vector pKT210. Micro-plasmid pCEL 44 is capable of transforming plant cells and rendering them resistant to hygromycin.

Strain CA19 is prepared as follows.

Figure 5:
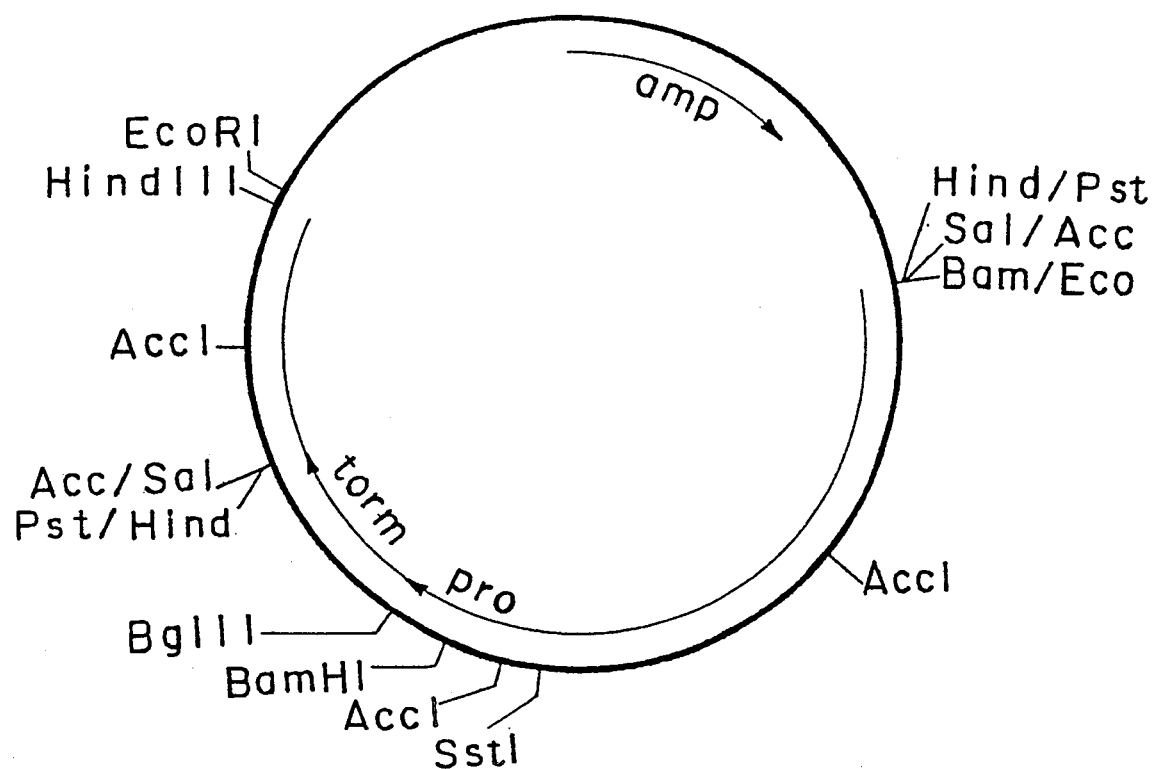
FIG. 5 is a restriction site and function map of plasmid pCEL30.

1. Culture of *Escherichia coli* RR1ΔM15/pCEL30 and Isolation of Plasmid pCEL30: Plasmid pCEL30 comprises the right-hand border sequence of the T-DNA and 5' end of the octopine synthase (ocs) gene derived from plasmid pTiA66. A linker containing a unique site is fused in the 11th codon of the ocs gene. Attached to the linker are the termination and polyadenylation signals of the hopaline synthase gene of plasmid pTiC58. Attached to these sequences is a sequence which includes the left-hand border sequence of the T-DNA derived from plasmid pTiA66. A restriction site and function map of plasmid pCEL30 is given in FIG. 5.

Plasmid pCEL30 can be conventionally isolated from *Escherichia coli* K12 RR1AM15/pCEDL30. *E. coli* RR1ΔM15/pCEL30 is on deposit at the Northern Regional Research Laboratory (NRRL), Peoria, Ill. 61604, and has accession number NRRL B-15915.

The isolation is performed as follows. *E. coli* RR1ΔM15/pCEL30 is grown in 750 ml of L medium (10 g/l caesin hydrolysate, 5 g/l yeast extract, 5 g/l NaCl, 1 g/l glucose, pH 7.4) containing ampicillin at 50 mg/ml according to conventional microbiological procedures. The culture is harvested after 24 hours incubation at 37° C. with vigorous shaking.

The culture is centrifuged, and the cell pellet is resuspended in 50 ml freshly-prepared lysis buffer (50 mM Tris-HCl, pH 8, 10 mM EDTA, 9 mg/ml glucose, 2 mg/ml lysozyme). After 45 minutes incubation on ice, the suspension is mixed with 100 ml of a solution that is 0.2N NaOH and 1% SDS. The suspension is then kept on ice for a further 5 minutes. Another 90 ml of 3M sodium acetate is added, and the mixture is maintained on ice for an additional 60 minutes.

Cell debris is removed by centrifugation, and the supernatant is mixed with 500 ml ethanol. After 2 hours at −20° C., nucleic acid is pelleted by centrifugation and is resuspended in 90 ml of 10 mM Tris-HCl, pH 8, 10 mM EDTA.

The nucleic acid solution is mixed with 90 gm cesium chloride, and 0.9 ml of a solution containing 10 mg/ml of ethidium bromide. This mixture is then centrifuged at 40,000 rpm for 24 hours to purify the plasmid DNA. The plasmid DNA band is recovered and is then recentrifuged at 40,000 rpm for 16 hours. The plasmid DNA band is again recovered and freed of cesium chloride and ethidium bromide by conventional procedures. It is next precipitated with 2 volumes of ethanol containing 90 g/l ammonium acetate. The pelleted DNA is dissolved in TE buffer (10 mM Tris-HCl, pH 8, 1 mM EDTA) at a concentration of 0.2 mg/ml.

2. Culture of *E. coli* JA221/pOW20 and Isolation of Plasmid pOW20: *E. coli* JA221/pOW20 is grown as described for *E. coli* RR1ΔM15/pCEL30 in part A1 of this example, and plasmid pOW20 is prepared as described for plasmid pCEL30 in part A1 of this example.

3. Construction of *E. coli* RR1ΔM15/pCEL40: Five μg of plasmid pCEL30 DNA are digested with 50 units of BglII restriction enzyme in a 150 μl reaction mixture of the composition recommended by the enzyme manufacturer. Restriction and other enzymes can be readily obtained from the following sources:

Bethesda Research Laboratories, Inc.
Box 6010
Rockville, Md. 20850
Boehringer Mannheim Biochemicals
7941 Castleway Drive
P.O. Box 50816
Indianapolis, Ind. 46250
New England Bio Labs., Inc.
32 Tozer Road
Beverly, Mass. 01915

Digestion is allowed to proceed for 90 minutes at 37° C.

The reaction mixture is first mixed with 8.75 μl of 0.5M Tris-HCl, pH 8, 1 mM EDTA and then with 1.25 units of calf intestinal phosphatase (which can be purchased from Boehringer Mannhelm) and incubated at 37° C. for 15 minutes. The mixture is next extracted with buffered phenol, then with ether and is precipitated with 2 volumes of ethanol containing ammonium acetate. After 30 minutes at −70° C., the DNA is pelleted and redissolved in TE buffer at a concentration of 10 μg/ml.

About 20 μg of plasmid pOW20 DNA is digested with the restriction enzymes BamHI and BglII according to the enzyme manufacturer's recommended procedures to obtain the aphIV gene. The aphIV gene is an *E. coli* gene which makes plants containing the gene resistant to hygromycin.

The DNA fragments resulting from this digestion are fractionated by conventional methods of agarose gel electrophoresis and isolated by entrapment on a piece of NA-45 DEAE paper (Schleicher & Schuell Inc., Keene, N.H. 03431) inserted into the gel during electrophoresis. DNA is eluted from the paper by spinning the paper for 5 seconds with a sufficient amount of a high salt buffer (1.0M NaCl; 0.1 mM EDTA; and 20 mM Tris, pH 8.0) to cover the paper in a microcentrifuge. The paper is incubated at 55°–60° C. for 10–45 minutes with occasional swirling. The buffer is removed, and the paper washed with about 50 μl of buffer. The DNA is extracted first with phenol and then with ether and is resuspended in TE buffer at a concentration of about 25 μg/ml.

Ten ng of the phosphatased, BglII-cut plasmid pCEL30 is mixed with 50 ng of the purified ~1.3 kb BamHI-BGlII fragment of plasmid pOW20 in a 15 μl ligase buffer (50 mM Tris-HCl pH 7.6; 10 mM MgCl$_2$; 10 mM DTT; and 1 mM ATP) containing 0.8 units of T4 DNA ligase (BRL). The mixture is incubated overnight at 15° C.

The ligation mixture is mixed with 15 μl sterile 60 mM CaCl₂ solution. Next, 70 μl of a suspension of competent *E. coli* RR1ΔM15 cells, which has been stored 20× concentrated in 30 mM CaCl₂, 15% glycerol at −70° C., are added. After 60 minutes on ice, the transformation mixture is heat-treated at 42° C. for 2 minutes and is then incubated with 0.5 ml L medium for 90 minutes at 37° C.

Samples of the mixture are spread on L medium containing ampicillin at 50 mg/l and solidified with agar at 15 g/l. These samples are then incubated overnight at 37° C. to permit growth of colonies from transformed cells.

Colonies resulting from the transformation are inoculated into 5 ml L medium containing ampicillin at 50 mg/ml and grown overnight at 37° C. Plasmid DNA is prepared from 1 ml samples of these cultures by the procedure of Holmes & Quigley, *Analytical Biochemistry*, 114, 193 (1981) and is redissolved in 50 μl of TE buffer.

4. Construction of Micro-Ti Plasmid pCEL44: Since plasmid pCEL40 is not capable of replication in Agrobacterium the micro T-DNA of plasmid pCEL40 was first transferred, as an EcoRI fragment, into broad-host-range vector pKT210. This broad-host-range vector is available from Plasmid Reference Center, Stanford University, Palo Alto, Calif. 94305.

Five μg of plasmid pKT210 are digested with 50 units of EcoRI restriction enzyme in a 150 μl reaction of a composition recommended by the enzyme manufacturer. After 90 minutes at 37° C., the reaction is treated with calf intestinal phosphatase as described above in part A3 of this example and is dissolved in TE buffer at a concentration of 10 μg/ml.

Fifteen μl of a preparation of plasmid pCEL40 DNA, grown as described above in part A3 of this example, are digested with 10 units of EcoRI restriction enzyme in a 20 μl reaction at 37° C. for 90 minutes and are then extracted with phenol, followed by extraction with ether. The digested DNA is precipitated with 2 volumes of ethanol containing ammonium acetate at −20° C. and is redissolved in 20 μl TE buffer.

Ten ng of phosphatased, EcoRI-cut pKT210 are ligated with 5 μl of ECoRI-cut pCEL40 as described above in part A3 of this example, and transformed into *E. coli* RR1ΔM15as described above in part A3 of this example.

Figure 6:
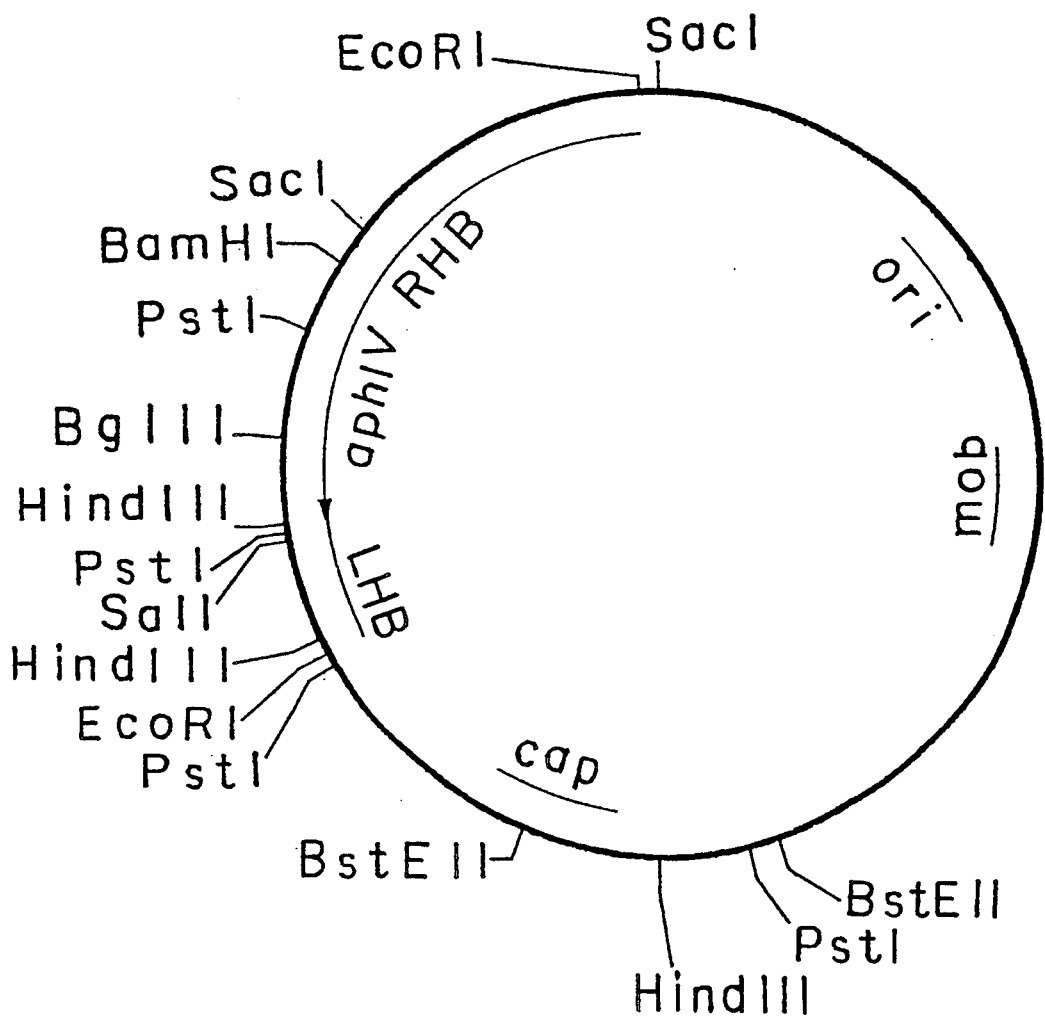
FIG. 6 is a restriction site and function map of plasmid pCEL44.

Transformed cells containing pCEL44 are selected by their ability to grow on solidified L medium containing chloramphenicol at 10 mg/l. A restriction site and function map of pCEL44 is provided in FIG. 6.

5. Conjugation of pCEL44 Into *A. tumefaciens* LBA4013 to form Strain CA19: *E. coli* K12 RR1ΔM15/pCEL44 and *E. coli* pRK2013 are grown overnight at 37° C. on solidified L medium. *A. tumefaciens* LBA4013 is grown for 2 days at 28° C. on solidified L medium.

One loop of *E. coli* K12 RR1ΔM15/pCEL44, one loop of *E. coli* pRK2013 and one loop of *A. tumefaciens* LBA 4013 are mixed in 1 ml of 30 mM magnesium sulfate solution. Next, a drop of the mixture is placed on solidified TY medium (5 g/l caesin hydrolysate, 5 g/l yeast extract, 15 g/l agar) and incubated at 28° C. overnight.

The bacterial growth is resuspended in 3 ml of 10 mM magnesium sulfate solution and 0.1 ml samples of serial dilutions are spread on solidified TY medium containing 100 mg/l nalidixic acid and 2 mg/l chloramphenicol and incubated at 28° C.

Transconjugants give rise to individual colonies after 2 to 4 days growth. These are inoculated singly into 25 ml liquid TY medium containing 100 mg/l nalidixic acid and 2 mg/l chloramphenicol and incubated at 28° C. with shaking for another 2 days. The plasmid content of the transconjugants is then checked by the method of Casse et al. (*Journal of General Microbiology* 113:229–242; 1979), and strain CA19 containing the wild type pTiAch5 plasmid and the pCEL44 plasmid is isolated.

The CA19 used to practice the method of the present invention was obtained from Clegg Waldron, Eli Lilly and Co., Indianapolis, Ind. The preparation of strain CA19 has also been described in Waldron et al., *Plant Molec. Biol.*, 5, 103 (1985) which is incorporated herein by reference.

B. Transformation Of Gladiolus

Corms of the Gladiolus cultivar Yellow Emperor were sterilized and cut into disks that were inoculated and incubated as described above in Example I, parts B and C, except that the disks were inoculated with strain CA19 rather than strain B6.

C. Results

1. Observations Of Disks: After 25 days of incubation, tumors are found to grow on the inoculated surface of the corm disks inoculated with vir+ *A. tumefaciens* strain CA19.

2. Assay of Tumors for Lysopine Dehydrogenase Activity: once the tumors reach 1 cm in size, they are assayed for enzyme activity as described above in Example I, part D. Octopine production in cell-free extracts of individual tumors growing on CA19-inoculated corm disks is found, showing that the tumors contain lysopine dehydrogenase and that the corm tissue is transformed.

3. Assay of Tumors for Hygromycin Resistance: Portions of the tumors produced on corm disks inoculated with strain CA19 are assayed for resistance to hygromycin as follows. The tumors are cut into approximately 3 mm cross sections which are cultured for three weeks on Duncan's medium (described by Duncan et al. in *Planta*, 165, 322 (1985)) supplemented with 200 ug/ml each carbenicillin (Sigma) and vancomycin (Lilly) or on BN4 medium (Murashige and Skoog major and minor salts (described in *Physiol. Plant*, 15 473 (1962)), 4 mg/l 2,4-dichlorophenoxy acetic acid as auxin, 9 g/l Difco Bactoagar and 20 g/l sucrose) supplemented with 200 μg/ml each carbenicillin and vancomycin, in the dark, at 25° to 27° C., followed by another three-week passage on those antibiotics.

To test the response to hvgromycin of the tissue cultures derived from the tumors, either whole cross sections plus the tissue which grows up from the cross sections or 100 mg callus samples are placed onto about 50 ml of Duncan's medium or of BN4 medium supplemented with the aforementioned concentrations of vancomycin and carbenicillin and containing about 125 μg/ml of hygromycin B (Lilly) contained in Falcon 1005 Petri dishes. This test is read after three weeks of incubation in the dark at 27° C. by visually checking for growth. Using this test, positive growth phenotypes are recovered from cultures derived from tumors produced by CA19-inoculated corm disks, showing that the corm tissue is transformed by the heterologous hygromycin gene.

Example IX

A. Preparation of Bacteria

A single colony of the *A. tumefaciens* strain IIBNV6 was inoculated into YEB, and the bacteria were incubated as described above in Example I, part A, for strain B6. The IIBNV6 strain is an avirulent strain of *A. tumefaciens*. It was obtained from James and Barbara Lippincott, Northwestern University, Evanston, Ill. It has been described in B. Lippincott et al, *Journal Of Bacteriology*, 132, 824–31 (1977) and Kado et al., *Journal of Bacteriology*, 145, 1365–73 (1981).

B. Inoculation of Gladiolus

Corms of the Gladiolus cultivars Oscar, Carmen, White Prosperity, White Friendship, Yellow Emperor and Golden Monarch were sterilized, cut into disks, inoculated and incubated as described above in Example I, parts B and C, except that the corm disks were inoculated with strain IIBNV6 rather than strain B6.

C. Results

1. Observation of Disks: The corm disks were observed for up to six months after inoculation. No tumors were observed growing on the surface of any of the disks of any cultivar inoculated with vir− *A. tumefaciens* strain IIBNV6. On some disks, a layer of cells formed, but this layer of cells could be identified as a healing response rather than tumor formation.

We claim:

1. A method of producing a transformed Gladiolus plant comprising:
    removing a piece of tissue from a corm;
    inoculating the tissue with vir+ *Agrobacterium tumefaciens* strain;
    incubating the inoculated tissue until a tumor forms;
    culturing at least a portion of the tumor in hormone-free medium until a cormel forms; and
    growing the cormel to produce the transformed plant.

2. A method as defined in claim 1 in which the Gladiolus is the cultivar Oscar.

3. A method as defined in claim 1 in which *Agrobacterium tumefaciens* strain is B-6 or LBA 4013.

4. A method as defined in claim 1 in which the strain is C58.

* * * * *